(12) United States Patent
Rockwood, Jr. et al.

(10) Patent No.: US 6,508,840 B1
(45) Date of Patent: Jan. 21, 2003

(54) COLLARLESS SHOULDER ARTHROPLASTY PROSTHESIS

(75) Inventors: Charles A. Rockwood, Jr., San Antonio, TX (US); Jeffrey M. Ondrla, Leesburg, IN (US)

(73) Assignee: DePuy Orthopaedis, Inc., Warsaw, IN (US)

( * ) Notice: Subject to any disclaimer, the term of this patent is extended or adjusted under 35 U.S.C. 154(b) by 0 days.

(21) Appl. No.: 09/543,118

(22) Filed: Apr. 5, 2000

Related U.S. Application Data

(60) Provisional application No. 60/128,134, filed on Apr. 7, 1999.

(51) Int. Cl.[7] .............................. A61F 2/40; A61B 19/00
(52) U.S. Cl. ..................................... 623/19.12; 128/898
(58) Field of Search .......................... 623/18.11, 19.12, 623/19.13, 9.14, 22.11–22.14, 23.11–23.27; 128/898

(56) References Cited

U.S. PATENT DOCUMENTS

| | | | | |
|---|---|---|---|---|
| 3,965,490 A | * | 6/1976 | Murray et al. ................ | 3/1.913 |
| 4,287,617 A | * | 9/1981 | Tornier ........................ | 3/1.913 |
| 4,608,055 A | * | 8/1986 | Morrey et al. ................ | 623/23 |
| 5,171,288 A | | 12/1992 | Mikhail et al. | |
| 5,344,458 A | | 9/1994 | Bonutti | |
| 5,507,830 A | * | 4/1996 | DeMane et al. ............... | 623/23 |
| 5,509,935 A | * | 4/1996 | Fosco et al. .................. | 623/22 |
| 5,571,203 A | * | 11/1996 | Masini ......................... | 623/23 |
| 5,658,349 A | * | 8/1997 | Brooks et al. ................ | 623/23 |
| 5,728,161 A | * | 3/1998 | Camino et al. ............... | 623/19 |
| 6,120,544 A | * | 9/2000 | Grundei et al. ............... | 623/23 |
| 6,165,224 A | * | 12/2000 | Tornier ..................... | 623/23.21 |

* cited by examiner

*Primary Examiner*—Corrine McDermott
(74) *Attorney, Agent, or Firm*—Maginot, Moore & Bowman

(57) ABSTRACT

A shoulder prosthesis of the present invention includes a modular humeral prosthesis component employing a collarless design. A body portion of the prosthesis is provided without a collar, and it may be implanted into a prepared proximal end of a humerus such that the body sits recessed below the level of the cut proximal surface of the humerus. A head portion is provided in which a support surface of the head functions as collar by direct apposition of it to the cut proximal humerus. The modular connection is thus recessed below the proximal bone surface. By providing a modular connection which is recessed below the bone surface, the benefits of modularity may be retained, while joint overstuffing may be reduced or eliminated, and a substantially full range of motion may be achieved.

10 Claims, 3 Drawing Sheets

COLLARLESS SHOULDER ARTHROPLASTY PROSTHESIS

This application claims the benefit of U.S. Provisional Application Serial No. 60/128,134 which was filed on Apr. 7, 1999.

TECHNICAL FIELD OF THE INVENTION

The present invention relates to improvements in joint prostheses; more particularly to improvements in shoulder joint prostheses which employs a collarless design.

BACKGROUND OF THE INVENTION

Shoulder joint prostheses are known in the art. See, for example, U.S. Pat. Nos. 4,919,669 and 5,738,161, hereby incorporated by reference. A typical shoulder prosthesis comprises a body, which is for implantation into a prepared humerus, and a head, which is fixed to the body and provides a bearing surface. Modular shoulder prostheses are also known. See, for example, U.S. Pat. No. 5,314,479, hereby incorporated by reference. U.S. Pat. No. 5,314,479 discloses a modular prosthesis comprising a body, which is implanted into the humerus, and a head, which seats onto the body. The head and body can be selected independently of each other, and head/body combinations can be selected by a surgeon to provide a custom fit without carrying a large expensive inventory of prostheses. A typical modular shoulder prosthesis, such as that disclosed in U.S. Pat. No. 5,314,479, also has a collar located between the head and the body. The collar sits on the prepared proximal surface of the humerus and provides a suitable surface for supporting the head. The collar, however, occupies joint space, and as compared to an analogous prosthesis of a non-modular design, a modular prosthesis with a collar may require additional joint space. This additional joint space may cause "overstuffing" of the glenohumeral joint, resulting in a decrease in range of motion. Also known are modular designs which have a collar integral with the body and provide a "low profile" modular connection. See, for example, U.S. Pat. No. 5,489,309, hereby incorporated by reference. However, use of these prostheses still may result in overstuffing and a loss of useful articular surface.

SUMMARY OF THE INVENTION

The shoulder prosthesis of the present invention comprises a modular humeral prosthesis component employing a collarless design. A body portion of the prosthesis is provided without a collar, and it may be implanted into a prepared proximal end of a humerus such that the body sits recessed below the level of the cut proximal surface of the humerus. A head portion is provided in which a support surface of the head functions as collar by direct apposition of it to the cut proximal humerus. The modular connection is thus recessed below the proximal bone surface. By providing a modular connection which is recessed below the bone surface, the benefits of modularity may be retained, while joint overstuffing may be reduced or eliminated, and a substantially full range of motion may be achieved.

In an illustrated embodiment, the head and body are connected by a stem and socket arrangement known as a reverse morse taper design. In this illustrated embodiment, a tapered stem is provided on the head and positioned such that it extends away from the support surface. A mating socket is provided in the proximal surface of the body. Upon implantation, the tapered stem of the head seats and locks in the mating socket of the body. Because the proximal surface of the body is recessed from the proximal surface of the humerus, the space required by this modular connection is also recessed below the proximal surface of the humerus, and the modular connection does not occupy any joint space. Essentially the entire surface area of the prosthesis which is located above the cut proximal humeral bone surface may be useful articular surface area.

An alternative embodiment includes a standard taper design, in which a tapered stem extends from the body and mates with a socket located in the head. As with the reverse morse taper design, the modular connection is recessed below the proximal surface of the humerus and does not require joint space. Other coupling designs may be used and are within the scope and spirit of this invention.

Preferably, the prosthetic device of this invention is made of titanium or cobalt chrome. Alternatively, the prosthetic device of this invention can be made of other biocompatible materials which are of sufficient strength.

Additional features of the present invention will become apparent to those skilled in the art upon consideration of the following detailed description of preferred embodiments exemplifying the best mode of carrying out the invention as presently perceived.

Detailed Description of the Invention

Figure 1:
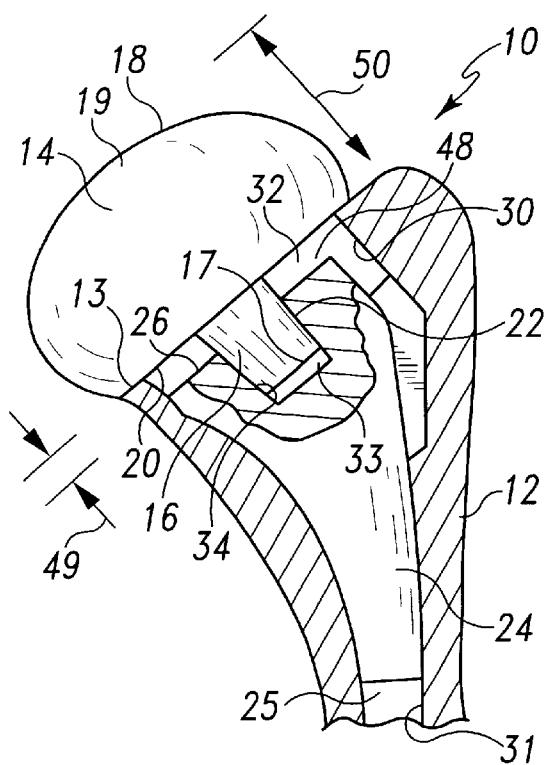
FIG. 1 is a cross-sectional view of a shoulder prosthetic device in accordance with this invention including a head and a body and employing a reverse morse taper design, with the prosthetic device shown implanted into a proximal end of a prepared humerus.

The present invention relates to a modular shoulder joint prosthetic device 10 which employs a collarless design. FIG. 1 shows a proximal end of a humerus 12 which has been prepared for joint replacement by removal of the natural humeral head (not shown): Prepared humerus 12, as shown in FIG. 1, has received prosthetic device 10 of this invention. Prosthetic device 10 is the humeral component of a prosthetic shoulder joint, and prosthetic device 10 comprises a body 24 and a head 14.

Still referring to FIG. 1, humerus 12, as prepared to receive prosthetic device 10, has a proximal bone surface 13 and an opening 32 extending through proximal bone surface 13 to a medullary passageway 31. Body 24 is seated within humerus 12 and has an elongated shaft 25 which extends into medullary passageway 31. As shown, body 24 is provided with a proximal surface 26 which is recessed below proximal bone surface 13. Humeral head 14 is secured to body 24. Humeral head 14 is provided with a support surface 20, which directly engages proximal bone surface 13. A bearing surface 18 of humeral head 14 provides the articulating surface of the shoulder joint prosthetic device 10 of this invention.

Figure 2:
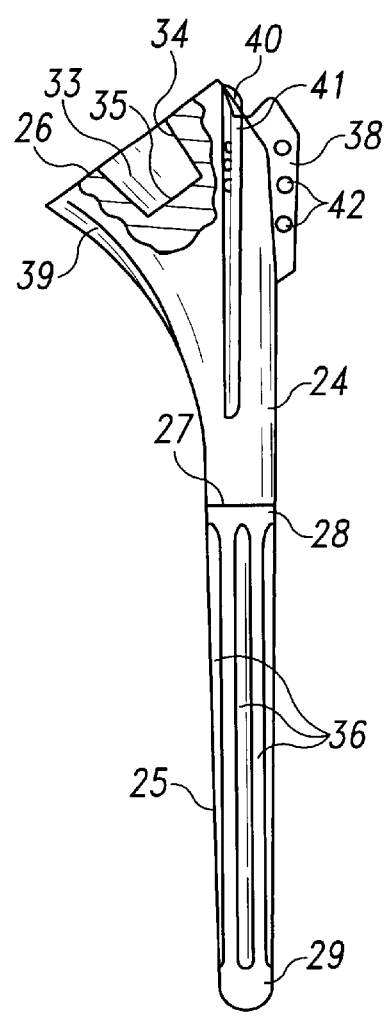
FIG. 2 is a front elevational view of the body of FIG. 1, with a cut-away illustrating a cavity for use in a reverse morse taper design, and showing an elongated shaft extending away from the distal end of the body.

Referring now to FIG. 2, body 24 of the illustrative embodiment is provided with proximal surface 26 and a distal end 27. A taper cavity 33 is formed in proximal surface 26 of body 24. Taper cavity 33 has a female taper 34, which gradually radially narrows nearer to a distal end 35 of taper cavity 33. Body 24 is shaped and sized to be received in opening 32 of humerus 12 and to be recessed from proximal bone surface 13, and taper cavity 33 is provided for attachment to head 14.

Still referring to FIG. 2, body 24 may be provided with various features which aid in providing proper alignment and secure placement within humerus 12. Shaft 25, with a proximal end 28 and a distal end 29, extends from distal end 27 of body 24 and is provided to extend into medullary passageway 31, as seen in FIG. 1. Shaft 25 may be provided as an integral extension of body 24. Alternatively, shaft 25 may be removable by threads or other connections and a variety of shafts of differing lengths may be provided. If removable, a variety of shafts 25 along with a variety of various sized heads 14 and bodies 24 would provide considerable modularity and would insure a more custom fit without requiring a large inventory of shoulder prostheses. Shaft 25 may be provided with a plurality of channels 36. Channels 36 may provide bone ingrowth sites, or if cement is used to secure body 24, channels 36 may provide areas for macro-interlock of bone cement. Also, for added stability and secure placement, body 24 may be provided with fins 38, 39, 40, and 41. Fins 38 and 41 are shown with a plurality of suture openings 42, but it will be understood that suture openings 42 may be placed on all fins 38, 39, 40, and 41. Suture openings 42 are useful in the repair of certain kinds of soft tissue injuries and disease.

Figure 3:
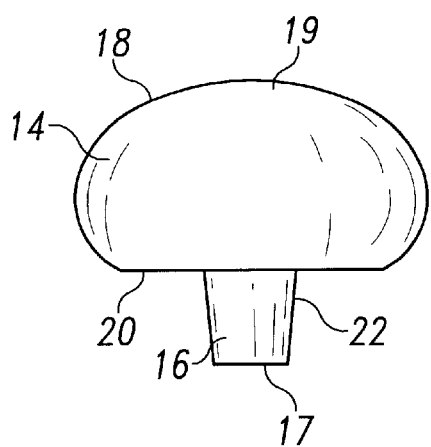
FIG. 3 is a front elevational view of the humeral head of FIG. 1, for use with the body of FIG. 2, showing a stem of a reverse morse taper design.

Now referring to FIG. 3, humeral head 14 of this embodiment includes support surface 20 for engaging proximal bone surface 13. Bearing surface 18 extends in a generally hemispherical shape from support surface 20, across a proximal end 19 of head 14, and back to support surface 20. In this illustrated embodiment, head 14 is provided with a taper stem 16 which extends distally away from support surface 20. Taper stem 16 includes a male taper 22 which gradually radially narrows as taper stem 16 extends away from support surface 20 toward a distal end 17 of taper stem 16. Taper stem 16 is positioned and designed to mate with taper cavity 33 of body 24.

Referring again to FIG. 1, humerus 12 has been prepared according to standard technique. Medullary passageway 31 has been prepared to accept shaft 25, and opening 32 has also been prepared to accept body 24. A canal 30 has been cut to accept lateral fin 38, and other fin tracks (not shown) may be cut to accept fins 39, 40, and 41. When body 24 is inserted into prepared humerus 12, shaft 25 enters medullary passageway 31 and fins 38, 39, 40, and 41 guide body 24 into proper position within opening 32. When body 24 is properly positioned, as shown in FIG. 1, proximal surface 26 of body 24 is recessed below proximal bone surface 13.

Still referring to FIG. 1, taper stem 16 of head 14 has been received in taper cavity 33, and tapers 22, 34 assure proper alignment between taper stem 16 and head 14. Tapers 22, 34 also provide a mechanical taper-lock connection, which secures head 14 to body 24. It will be appreciated, however, that one skilled in the art may find additional techniques for securing head 14 to body 24 or for supplementing this taper-lock connection without departing from the scope of this invention. As shown, distal end 17 of taper stem 16 does not engage distal end 35 of taper cavity 33. However, taper stem 16 may be positioned and shaped such that distal end 17 of taper stem 16 may engage distal end 35 of taper cavity 33. When head 14 and body 24 are locked together, support surface 20 of head 14 is positioned directly upon proximal surface 13 of humerus 12.

As seen in FIG. 1, when head 14 properly connects to body 24, a space 48 is formed between support surface 20 of head 14 and proximal surface 26 of body 24. A gap 49 illustrates the measurement of space 48, i.e. the distance between support surface 20 of head 14 and the proximal surface 26 of body 24. Space 48 is provided essentially within humerus 12 and does not occupy any significant joint space. A distance 50 between proximal bone surface 13 of humerus 12 and proximal end 19 of head 14 is about the same as such a distance would be in a comparable shoulder prosthesis of a non-modular design. Substantially all of bearing surface 18 would be useful articular surface area.

In modular prostheses with collars, the collar (not shown) may occupy a similar gap between the equivalent support surface of a head and a proximal end of a body. However, because such a collar would sit above the proximal surface of the humerus, the gap occupied by the collar would also occupy space in the glenohumeral joint without providing additional useful articular surface area, resulting in potential overstuffing of the joint. In the present invention, because space 48 is recessed and does not occupy the glenohumeral joint, the glenohumeral joint may not be overstuffed, and full range of motion may be obtained.

Figure 4:
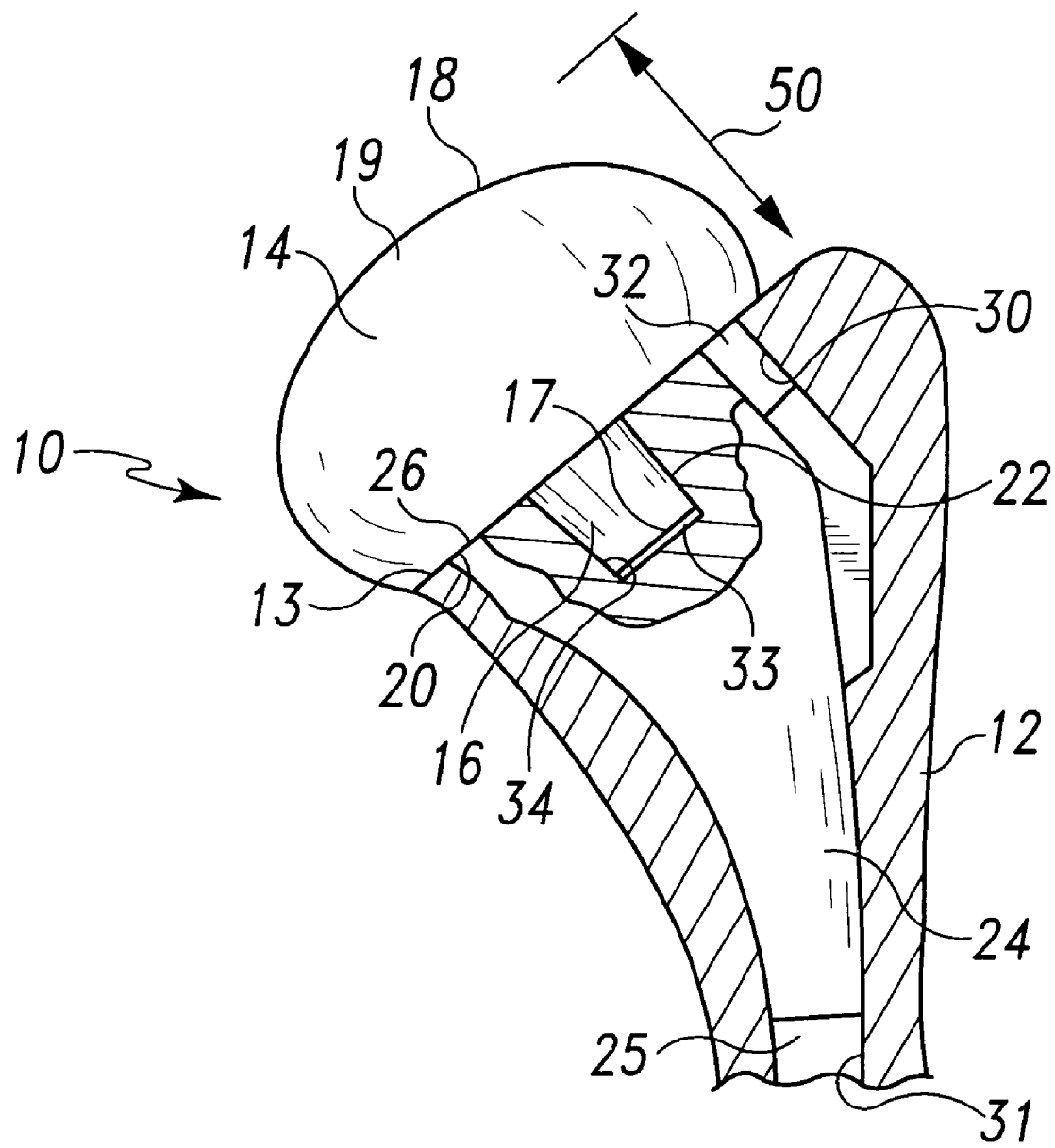
FIG. 4 is similar to FIG. 1, except showing an embodiment in which there is essentially no gap between the body and the head.

FIG. 4 illustrates an alternative embodiment of the prosthetic device 10 of this invention. In this embodiment, proximal surface 26 of body 24 is essentially flush with proximal bone surface 13. In such an embodiment, support surface 20 of head 14 would abut both proximal bone surface 13 and proximal surface 26 of body 24. Precise machining would permit taper stem 16 to fit within taper cavity 33 to provide a taper lock. Although there would be no space 48 in this embodiment, distance 50 would be essentially the same as illustrated in FIG. 1, and the prosthesis would occupy the same amount of space within the glenohumeral joint.

FIGS. 1–4 illustrate humeral joint prostheses 10 which employ a reverse taper design. As discussed above, in this design, stem 16 is located on the humeral head, rather than on the body, as in standard taper design seen below in FIGS. 5–7. Because there is no stem on the body portion, after the body is implanted into the humerus, this design allows relatively free access to the glenoid. However, as discussed below, the prosthesis of this invention may also employ a standard taper design.

Figure 5:
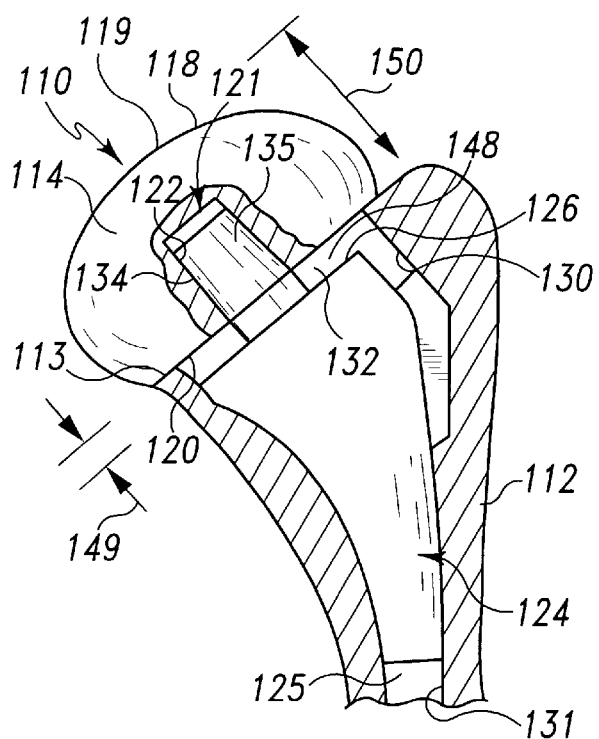
FIG. 5 is similar to FIG. 1, but showing an embodiment of a prosthetic device having a standard taper design.
Figure 7:
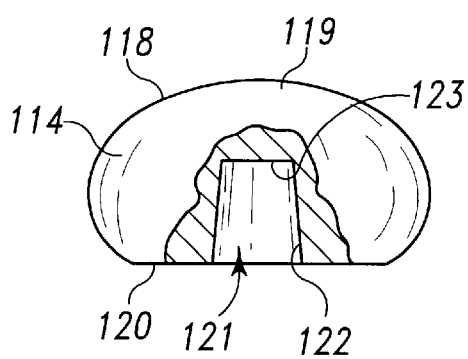
FIG. 7 is similar to FIG. 3, but with a cut-away showing a cavity for engaging the stem of FIG. 6.
Figure 6:
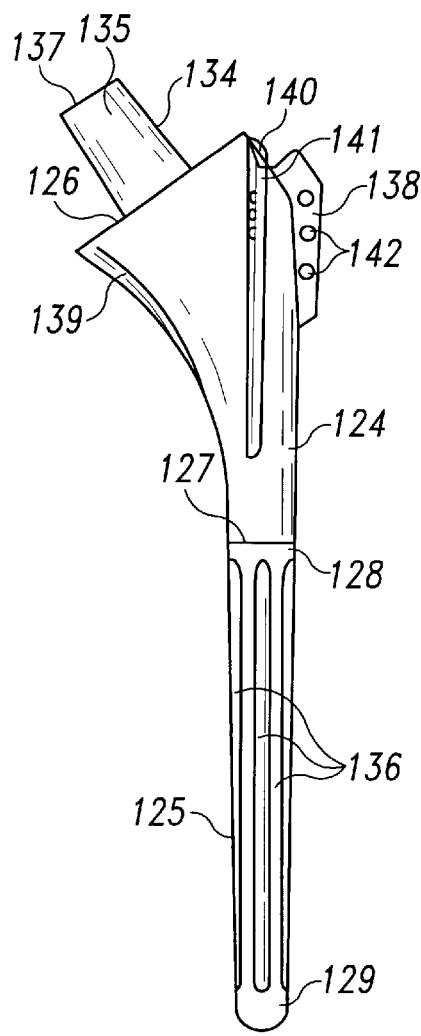
FIG. 6 is a front elevational view of the body shown in FIG. 5, illustrating the stem of a standard taper design.

FIGS. 5–7 illustrate an embodiment of the present invention employing a standard taper design. FIG. 5 shows a head 114 and a body 124 of this alternative embodiment, as they would appear when implanted onto a humerus 112. Humerus 112 is prepared in much the same way as described for FIG. 1, with a cut proximal bone surface 113 and an opening 132 extending through proximal bone surface 113 to a medullary passageway 131. Body 124 is similarly shaped and sized to be received in opening 132 and to be recessed from proximal bone surface 113. Body 124 is shown engaged with head 114. The overall external dimensions of a prosthetic device 110 shown in FIG. 5 are essentially the same as prosthetic device 10 shown in FIG. 1.

However, as can be seen in FIGS. 5 and 6, body 124 is provided with a taper stem 135, which extends from a proximal surface 126 of body 124. Taper stem 135 terminates in a proximal end 137. Taper stem 135 is provided with a male taper 134, which gradually radially narrows toward proximal end 137. The rest of body 124 is similar to body 24 shown in FIG. 2. As with body 124 is provided with a proximal surface 126, and a distal end 127. An elongated shaft 125, with a proximal end 128, a distal end 129 and a plurality of channels 136, is appended to distal end 127 of body 124. Body 124 is provided with a plurality of fins 138, 139, 140, 141, which may be provided with a plurality of suture openings 142. When inserted into prepared humerus 112, fins 138, 139, 140, 141 may engage fin tracks such as a canal 130, which is positioned to engage lateral fin 138.

As best seen in FIGS. 5 and 7, head 114 is provided with a taper cavity 121. Taper cavity 121 is provided with a proximal end 123, and a female taper 122 which gradually radially narrows toward proximal end 123. Head 114 is provided with a generally hemispherical bearing surface 118, which extends from a support surface 120, through a proximal end 119, and extends back to support surface 120. Bearing surface 118 is similar to bearing surface 18 shown in FIG. 2.

As best seen in FIG. 5, taper stem 135 of body 124 is positioned. and designed to engage in a mechanical taper-lock connection with taper cavity 121 of head 114. Although in opposite orientation, taper stem 135 and taper cavity 121 provide a similar connection to that of taper stem 16 and taper cavity 33 shown in FIG. 1. As seen in FIG. 5, body 124 is implanted into humerus 112 such that proximal surface 126 of body 124 is recessed beneath proximal bone surface 113. A space 148, illustrated by a gap 149, separates proximal surface 126 of body 124 from support surface 120 of head 114. A distance 150 between proximal bone surface 113 of humerus 112 and proximal end 119 of head 114 is about the same as distance 50 shown in FIG. 1. Although taper stem 135 and taper cavity 121 of this embodiment are in opposite orientation relative to the embodiment described above in FIGS. 1–3, space 148 is similarly recessed within humerus 112 and prosthetic device 110 of this invention occupies essentially the same joint space as prosthetic device 10 described above. Thus, as with the embodiment illustrated in FIG. 1, the entire bearing surface 118 may provide articular surface area.

While the reverse morse taper and standard taper designs are illustrated above, other mechanisms for coupling the head to the body may be employed and still remain within the scope and spirit of this invention.

Surgical techniques for implantation of a shoulder prosthesis are well known in the art. A surgical procedure similar to that referenced in U.S. Pat. No. 5,314,479 may be used with the prosthesis of this invention. Only a slight modification may be required in which the opening through the cut proximal surface of the humerus is cut deeper in order to receive the body and to permit the body to sit recessed from the cut proximal surface of the humerus. The shoulder prosthesis of this invention may be used with glenoid components which are known in the art. See, for example U.S. Pat. No. 5,032,132, hereby incorporated by reference. These surgical techniques may be amended to allow for locking head 14 or 114 to body 39 or 139 prior to inserting body 39 or 139 into humerus 12 or 112.

Although the invention has been described in detail with reference to a preferred embodiment, variations and modifications exist within the scope and spirit of the invention as described and defined in the following claims.

What is claimed is:

1. A method for implanting a modular shoulder joint prosthesis into a humerus having a prepared proximal bone surface and a prepared opening therein, comprising the steps of:

providing a plurality of bodies, each body having a proximal surface, with a cavity extending distally therein, and a distal end having an elongated shaft extending distally therefrom, providing a plurality of heads, each head having a bearing surface, a support surface, and a stem extending distally from the support surface, the stem being positioned and sized to form a modular connection with the cavity of a selected body, selecting a body to fit within the prepared opening such that the proximal surface of the body is recessed from the proximal bone surface of the humerus, and selecting a head to connect with the body such that, upon forming the modular connection, the support surface is in contact with the prepared proximal bone surface.

2. The method of claim 1 for implanting a modular shoulder joint prosthesis into a humerus, wherein the modular connection is a taper lock.

3. The method of claim 2 for implanting a modular shoulder joint prosthesis into a humerus, wherein the elongated shaft is removably fixed to the distal end of the body and the method further comprises the step of:

replacing the elongated shaft with a second elongated shaft of a different size.

4. The method of claim 1 for implanting a modular shoulder joint prosthesis into a humerus, wherein the method further comprises the steps of:

inserting the selected body into the prepared opening of the prepared humerus, and forming a modular connection between the selected head and the inserted selected body.

5. The method of claim 1 for implanting a modular shoulder joint prosthesis into a humerus, wherein the method further comprises the steps of:

forming a taper lock between the selected body and the selected head to form a complete humeral implant, and inserting the complete humeral implant into the prepared opening in the humerus.

6. A method for implanting a prosthesis into a bone having a prepared proximal bone surface and a prepared opening therein, comprising the steps of:

selecting a body having a proximal surface and a cavity extending distally therein to fit within the prepared opening with said proximal surface recessed from the prepared proximal bone surface;

implanting the body within the opening with said proximal surface recessed from the prepared proximal bone surface;

selecting a head having a bearing surface, a support surface and a stem extending distally from said support surface; and forming a modular connection between the stem and the cavity of the body to connect the head to the body such that said support surface is in contact with the prepared proximal bone surface.

7. The method of claim 6, wherein the modular connection is a taper lock.

8. The method of claim 6, wherein the bone is the humerus and the bearing surface is configured for positioning within the glenohumeral joint space.

9. The method of claim 6, wherein the step of forming the modular connection is performed after the step of implanting the body within the opening in the bone.

10. The method of claim 6, wherein:

the step of forming the modular connection is performed before the step of implanting the body within the opening in the bone; and the step of implanting the body within the opening in the bone includes implanting the body until said support surface is in contact with the prepared proximal bone surface.

* * * * *